United States Patent
Kim et al.

(10) Patent No.: US 10,603,254 B2
(45) Date of Patent: *Mar. 31, 2020

(54) URETHANE FOAM FOR USE IN IMPREGNATING COSMETIC COMPOSITION

(71) Applicant: AMOREPACIFIC CORPORATION, Seoul (KR)

(72) Inventors: Kyung Nam Kim, Yongin-si (KR); Jung Sun Choi, Yongin-si (KR); Min Kyung Shim, Yongin-si (KR); Kyung Ho Choi, Yongin-si (KR); Yeong Jin Choi, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/678,446

(22) Filed: Nov. 8, 2019

(65) Prior Publication Data

US 2020/0069536 A1 Mar. 5, 2020

Related U.S. Application Data

(63) Continuation of application No. 14/034,650, filed on Sep. 24, 2013, now Pat. No. 10,537,500, which is a continuation-in-part of application No. PCT/KR2012/002141, filed on Mar. 23, 2012, application No. 16/678,446, which is a continuation of application No. 16/221,583, filed on Dec. 17, 2018, now Pat. No. 10,537,501, which is a continuation-in-part of application No. 14/034,650, filed on Sep. 24, 2013, now Pat. No. 10,537,500, which is a continuation-in-part of application No. PCT/KR2012/002141, filed on Mar. 23, 2012.

(30) Foreign Application Priority Data

Mar. 24, 2011 (KR) .................. 10-2011-0026466

(51) Int. Cl.

| | |
|---|---|
| *A61K 8/02* | (2006.01) |
| *A61K 8/87* | (2006.01) |
| *A61Q 1/00* | (2006.01) |
| *A61Q 1/02* | (2006.01) |
| *A61Q 1/04* | (2006.01) |
| *A61Q 1/06* | (2006.01) |
| *A61Q 1/08* | (2006.01) |
| *A61Q 1/10* | (2006.01) |
| *A61Q 17/04* | (2006.01) |
| *C08L 75/06* | (2006.01) |
| *C08L 75/08* | (2006.01) |
| *C08G 101/00* | (2006.01) |

(52) U.S. Cl.
CPC .......... *A61K 8/0216* (2013.01); *A61K 8/0208* (2013.01); *A61K 8/87* (2013.01); *A61Q 1/00* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 17/04* (2013.01); *C08L 75/06* (2013.01); *C08L 75/08* (2013.01); *C08G 2101/00* (2013.01)

(58) Field of Classification Search
CPC ...... A61K 8/0216; A61K 8/0208; A61K 8/87; A61Q 1/00; A61Q 1/04; A61Q 1/06; A61Q 1/08; A61Q 1/10; A61Q 1/02; A61Q 17/04; C08L 75/06; C08L 75/08; C08G 2101/00

See application file for complete search history.

(56) References Cited

U.S. PATENT DOCUMENTS

| | | |
|---|---|---|
| 1,851,462 A | 10/1932 | Steller |
| 2,204,203 A | 6/1940 | Zimmerman |
| 2,764,565 A | 9/1956 | Hoppe et al. |
| 3,133,309 A | 5/1964 | Miles |
| 3,171,820 A | 3/1965 | Volz |
| 3,463,745 A | 8/1969 | Hofrichter et al. |
| 3,465,759 A | 9/1969 | Haefele |
| 3,475,525 A | 10/1969 | Peters |
| 3,748,288 A | 7/1973 | Winkler et al. |
| 3,799,898 A | 3/1974 | Lamplugh et al. |
| 3,949,137 A | 4/1976 | Akrongold et al. |
| 4,130,121 A | 12/1978 | Wetzel |
| 4,165,815 A | 8/1979 | Vetter |
| 4,259,452 A | 3/1981 | Yukuta et al. |
| 4,271,272 A | 6/1981 | Strickman et al. |
| 4,309,509 A | 1/1982 | Wood |
| 4,323,656 A | 4/1982 | Strickman et al. |
| 4,344,930 A | 8/1982 | Macrae et al. |
| 4,374,935 A | 2/1983 | Decker et al. |
| 4,427,798 A | 1/1984 | Konig et al. |

(Continued)

FOREIGN PATENT DOCUMENTS

| | | |
|---|---|---|
| BE | 875638 | 8/1979 |
| CN | 101977587 A | 2/2011 |

(Continued)

OTHER PUBLICATIONS

International Search Report with English Translation for International Application No. PCT/KR2015/003646 dated Jul. 21, 2015.

(Continued)

*Primary Examiner* — Hasan S Ahmed

(74) *Attorney, Agent, or Firm* — Rothwell, Figg, Ernst & Manbeck, P.C.

(57) ABSTRACT

Provided is a polyether-based urethane foam for impregnating a cosmetic composition. The polyether-based urethane foam has excellent touch feel, portability and stability.

34 Claims, 14 Drawing Sheets

(56) References Cited

U.S. PATENT DOCUMENTS

| | | |
|---|---|---|
| 4,440,181 A | 4/1984 | Scherer |
| 4,537,912 A | 8/1985 | Griswold |
| 4,594,835 A | 6/1986 | Gray |
| 4,656,196 A | 4/1987 | Kelly et al. |
| 4,706,693 A | 11/1987 | Spector |
| 4,806,572 A | 2/1989 | Kellett |
| 4,906,672 A | 3/1990 | Stone et al. |
| 4,985,467 A | 1/1991 | Kelly et al. |
| 5,064,653 A | 11/1991 | Sessions et al. |
| 5,065,752 A | 11/1991 | Sessions et al. |
| 5,098,621 A | 3/1992 | Hermann |
| 5,296,518 A | 3/1994 | Grasel et al. |
| 5,486,167 A | 1/1996 | Dragoo et al. |
| 5,552,449 A | 9/1996 | Sollers et al. |
| 5,591,779 A | 1/1997 | Bleys et al. |
| 5,702,713 A | 12/1997 | Joulia |
| 5,762,946 A | 6/1998 | Gueret |
| 5,961,961 A | 10/1999 | Dodkowski et al. |
| 6,271,277 B1 | 8/2001 | Bleys et al. |
| 6,371,606 B1 | 4/2002 | Free |
| 6,391,233 B1 | 5/2002 | Otani et al. |
| 6,638,986 B2 | 10/2003 | Falke et al. |
| 6,706,775 B2 | 3/2004 | Hermann et al. |
| 7,427,412 B1 | 9/2008 | Painter et al. |
| 7,612,160 B2 | 11/2009 | Nguyen-Kim et al. |
| 7,811,021 B2 | 10/2010 | Gueret |
| 8,367,083 B2 | 2/2013 | Barba et al. |
| 8,784,854 B2 | 7/2014 | Choi et al. |
| 9,532,637 B2 | 1/2017 | Choi et al. |
| 2002/0182245 A1 | 12/2002 | Thomson |
| 2004/0170670 A1 | 9/2004 | Smith et al. |
| 2005/0159500 A1 | 7/2005 | Dreier et al. |
| 2006/0210612 A1 | 9/2006 | Simon |
| 2006/0235100 A1 | 10/2006 | Kaushiva et al. |
| 2007/0189975 A1 | 8/2007 | Thomson |
| 2007/0277844 A1 | 12/2007 | Gueret |
| 2009/0018224 A1 | 1/2009 | Niesten et al. |
| 2009/0047495 A1 | 2/2009 | Hubbs |
| 2009/0197948 A1 | 8/2009 | Miyahara et al. |
| 2011/0014254 A1 | 1/2011 | Choi et al. |
| 2014/0023689 A1 | 1/2014 | Kim et al. |
| 2014/0341959 A1 | 11/2014 | Choi et al. |
| 2015/0078802 A1 | 3/2015 | Choi et al. |
| 2015/0117931 A1 | 4/2015 | Jung et al. |
| 2015/0118269 A1 | 4/2015 | Choi et al. |
| 2015/0196468 A1 | 7/2015 | Kim et al. |

FOREIGN PATENT DOCUMENTS

| | | |
|---|---|---|
| DE | 2356460 | 5/1974 |
| EP | 0528705 | 9/2000 |
| EP | 2425961 A1 | 3/2012 |
| EP | 2837305 | 2/2015 |
| EP | 2837305 A1 | 2/2015 |
| EP | 2837374 A1 | 2/2015 |
| GB | 1498363 | 1/1978 |
| JP | S6272732 A | 4/1987 |
| JP | H09220118 A | 8/1987 |
| JP | 1988196612 | 12/1988 |
| JP | 1988199706 | 12/1988 |
| JP | 02080257 U | 6/1990 |
| JP | 08164019 A | 6/1996 |
| JP | 08266329 A | 10/1996 |
| JP | 08325125 A | 12/1996 |
| JP | 3015878 B2 | 3/2000 |
| JP | 200079016 A | 3/2000 |
| JP | 8187673 B2 | 5/2001 |
| JP | 2002-53640 A | 2/2002 |
| JP | 200312457 | 1/2003 |
| JP | 2003012457 A | 1/2003 |
| JP | 2003192826 | 7/2003 |
| JP | 2003199425 | 7/2003 |
| JP | 2003231197 | 8/2003 |
| JP | 2004267277 A | 9/2004 |
| JP | 2005-152186 A | 6/2005 |
| JP | 2006241150 A | 9/2006 |
| JP | 2007508086 A | 4/2007 |
| JP | 2007330771 A | 12/2007 |
| JP | 2009019008 A | 1/2009 |
| JP | 2010-6294 A | 1/2010 |
| JP | 4588357 B2 | 12/2010 |
| JP | 2011132154 | 7/2011 |
| JP | 2011132154 A | 7/2011 |
| KR | 0131075 | 11/1997 |
| KR | 100498655 B1 | 7/2005 |
| KR | 1020090100643 A | 9/2009 |
| KR | 1020130083852 A | 7/2013 |
| KR | 10-2013-0116043 | 10/2013 |
| KR | 1020130116043 A | 10/2013 |
| KR | 1020130116044 A | 10/2013 |
| KR | 1020130116182 A | 10/2013 |
| KR | 1020130116205 A | 10/2013 |
| KR | 1020140038880 A | 3/2014 |
| KR | 1020150063196 A | 6/2015 |
| WO | 9221448 A1 | 12/1992 |
| WO | 9947127 A1 | 9/1999 |
| WO | 2005039350 A1 | 6/2005 |
| WO | 2008112139 | 9/2008 |
| WO | 2009116817 A2 | 9/2009 |
| WO | 2012128589 A2 | 9/2012 |

OTHER PUBLICATIONS

Japanese Office Action—Japanese Application No. 2016-561816 dated Jun. 12, 2018, citing references listed within.
Supplementary European Search Report for Application No. 15776533.0 dated Dec. 19, 2017.
Written Opinion for International Application No. PCT/KR2015/003646 dated Jul. 21, 2015.
Written Opinion for International Application No. PCT/KR2013/003101 dated Jul. 3, 2013.
Japan Office Action Corresponding Patent Application No. JP 2015505648 dated Mar. 10, 2017, with Partial English Translation.
International Search Report for International Application No. PCT/KR2013/003101 dated Jul. 3, 2013.
Non-Final Office Action dated Apr. 21, 2016 in KCL0204US.
Non-Final OA dated Dec. 7, 2017 in KCL0204USC.
Non-Final Office Action dated Nov. 25, 2016 in KCL0204US.
Alain Parfondry, "Polyurethane Technology & Applications", 15 pages, Nov. 2002.
Declaration of R. Randall Wickett, Petition for Inter Partes Review of U.S. Pat. No. 8,784,854 under U.S.C. §§311-319 and 37 C.F.R. §§42.1-.8, 42.100-,123, Jul. 27. 2018, 90 pages.
The HLB System, a time-saving guide to emulsifier selection, 22 pages, Mar. 1980.
Declaration of Robert Y. Lochhead, Ph.D., FRSC, Case IPR2018-01516, U.S. Pat. No. 8,784,854 B2, dated Nov. 30, 2018, 185 pages.
Petition for Inter Partes Review of U.S. Pat. No. 8,784,854 under U.S.C. §§311-319 and 37 C.F.R. §§42.1-.8; 42.100-.123, dated Aug. 6, 2018, 78 pages.
Patent Owner's Preliminary Response, Case IPR2018-01516, U.S. Pat. No. 8,784,854 B2, dated Nov. 30, 2018, 70 pages.
Decision: Denying Institution of Inter Partes Review 35 U.S.C. § 314(a), Case IPR2018-01516, U.S. Pat. No. 8,784,854 B2, Feb. 20, 2019, 29 pages.
Decision of Intellectual Property Trial and Appeal Board, 6th Department, Trial No. 2018Dang (decision reversing the original decision)76.
Decision of Inteliectual Property Trial and Appeal Board, 7th Department, Trial No. 2018Jeong49.
Decision of Patent Court, 1st Dvision, Case No. 2016Heo8667 Invalidation of Registration (Patent).
Decision of Supreme Court, 1st Division, Case No. 2018Hu10596 Invalidation of Registration (Patent).
Kamicokrolock, "Review, Etude house Cushion Foundation", website contents, Mar. 14, 2015, 3 pages.
Merquinsa, Polyurethane Types, Web site contents, pp. 1-8.
Meyer R. Rosen (ed.), Delivery System Handbook for Personal Care and Cosmetic Products, 2005, pp. 513-525.

(56) References Cited

OTHER PUBLICATIONS

Michael Szycher, Szycher's Handbook of Polyurethanes, 1999, p. 7-6.
Michael Szycher, Szyoher's Handbook of Polyurethanes, 1999, pp. C-8, 21, and 24.
Mihail Ionescu, "Chemistry and Technology of Polyols for Polyurethanes", 2005, pp. 2-4, 49-50, 263, 538-540, 547, Rapra Technology Limited.
Polyurethane Technology & Applications, pp. 107-108.
Polyurethane Technology & Applications, pp. 311-330.
Polyurethane Technology & Applications, pp. 3-5, 89-90, 123, 125, 169-171, 223-226.
Seong-Mi Park, Researcher's Statement, COSMAX R&I Institute, Apr. 17, 2017, 1 page.
T. Thomson, Design and Applications of Hydrophilic Polyurethanes, 2000, pp. 1-9, Preface xi-xiii.
Test Result Sheet, "Stability Test of LLBB Cushion", Korea Conformity Laboratories, 2017, pp. 1-5.
www.ifacemaker.com, a review on ALMAY Nearly Naked Foundation, May 29, 2003.
Tony Abisaleh et al., "Polyurethane Technology & Applications", 18 pages.
Result report of reproduction experiments on Amorepacific's patent (No. 1257628), 2017, 21 pages.
Reticulated foam, Edited on Jun. 3, 2018, pp. 1-3, Retrieved from the Internet Jun. 15, 2018 <URL:https://en.wikipedia.org/wiki/Reticulated_foam>.
"Reticulated Polyurethane Foam", UFP Technologies, Retrieved from the Internet Jul. 8, 2016, pp. 1-3.
Reticulated Foam, Australian Foam Manufacturer, Joyce Foam Products, Retrieved from the Internet Nov. 10, 2016, <URL: http://www.joyce.com.au/foams/reticulatedfoam/>.
Seong-Mi Park, "Report on Stability Test of Sponge Impregnated with LLBB Cushion Cosmetic Composition", Cosmax R&I Institute, Apr. 19, 2017, pp. 1-5, Korea.
Sang-Beom Kim, "About Structure and Properties of Polyurethane Foam", Letter of Opinion, May 9, 2016, pp. 1-4.
Shimin Wu, et al., "Concise Dictionary of Fine Chemicals", Shenyang: Liaoning Science and Technology, (Jun. 1999), pp. 1-7.
Singaporean Written Opinion—Application No. 201209361-3 dated Sep. 9, 2013, citing previous filed references.
Taiwanese Office Action—TW Application No. 101109975 dated Jan. 13, 2014, citing previous filed references.
Taiwanese Office Action—TW Application No. 101109975 dated Feb. 10, 2014, citing previous filed references.
UFP Technologies—Reticulated Foam, (Copyright 2011), pp. 1-2, Retrieved from the Internet Sep. 2, 2015, <URL: http://www.ufpt.com/>.
Written Opinion for International Application No. PCT/KR2012/002141 dated Oct. 31, 2012.
"100% Open Cell Flexible Polyurethane Foams", FXI Reticulated Foams, Product Sheet, FXI, Inc., Retrieved from the Internet Nov. 22, 2016, 1 page, <URL: fxi.com>.
"BB Cushion Sponge is Melting", Posted on the Internet Feb. 4, 2015, <URL: http://www.todayhumor.co.kr/board/view.php?table=fashion&no=142195>.
"Filters for Fishkeeping", EMW filtertechnik, Product Brochure, Retrieved from the Internet Nov. 22, 2016, pp. 1-4, <URL: www.emw.de>.
"Nature Republic CC Cushion Pact Sponge Gets Melted!!", Posted on the Internet Feb. 5, 2015, <URL: http://blog.haver.com/clawsome/220263606984>.
"Reticulated (Open-Cell) & Non-Reticulated (Closed-Cell) Foam Swabs", Berkshire, Retrieved from the Internet Nov. 11, 2016, pp. 1-5, <URL: http://www.berkshire.com/shop/cleanroomcleaningswabs/foam.html>.
"Reticulated Foam" and "Open Cell Polyurethane Foam", Foam Engineers Limited, Retrieved from the Internet Jul. 8, 2016, pp. 1-2, <URL: http://www.foamengineers.co.uk/foammanufacturingsuppliers/reticulated-foam>.
"Reticulated Foam-Polyurethane-based foam with open cellular structure", Material Sample Shop.Com, Retrieved from the Internet Jul. 8, 2016, pp. 1-2, <URL: https://www.materialsampleshop.com/products/reticulatedfoampolyurethane-based-foam-with-open-cellular-structure>.
"Reticulated Open Cell Black Packaging Foam with Polyester Polyurethaner Material", Changzhou Dayetengfei Sponge Factory, Retrieved from the Internet Jul. 8, 2016, pp. 1-3, <URL: http://www.customizedfoam.com/sale-7566632-reticulatedopen-cellblack-packaging-foam-with-polyesterpolyurethaner-material.html>.
"Reticulated Polyurethane Foam", FXI Innovations, Retrieved from the Internet Nov. 11, 2016, pp. 1-3, <URL: http://fxi.com/foamtechnologies/processes/reticulation.php>.
"Reticulated Polyurethane Foam", UFP Technologies, Retrieved from the Internet Jul. 8, 2016, pp. 1-3, <URL: http://www.ufpt.com/materials/foam/reticulatedpolyurethane-foam.html>.
"Reticulated Polyurethane Foam: Quenching vs. Zapping", UFP Technologies, Retrieved from the Internet May 12, 2016, <URL: http://www.ufpt.com/resource-center/quenching-vs-zappingreticulated-polyurethane/>.
"Trend of Global Urethane Raw Materials and Products Market", KIET Overseas Industrial Information, Retrieved from the Internet Nov. 15, 2016, pp. 1-2, <URL: http://www.kiet.go.kr/servlet/isearch?mode=view&dataNo=43619>.
"Optimization Technology Support for Polyurethane Foam Production through Analysis of Correlations Between CellStructure and Properties", Ministry for Commerce, Industry and Energy, Sep. 30, 2003, pp. 8, 11 and 12, KR.
Canadian Office Action for corresponding Canadian Patent Application No. 2,804,298 dated Jan. 18, 2017, citing previously filed reference.
Canadian Office Action for corresponding Canadian Patent Application No. 2,804,298 dated Jan. 4, 2016, citing U.S. Pat. No. 3,133,309 and previously filed references.
Canadian Office Action for corresponding Canadian Patent Application No. 2,804,298 dated Sep. 12, 2016.
Canadian Office Action—Canadia Application No. 2804298 dated May 29, 2014.
Canadian Office Action—Canadia Application No. 2804298 dated Oct. 28, 2013.
Canadian Office Action—Canadian Application No. 2804298 dated May 6, 2015, citing U.S. Pat. No. 3,133,309.
Canadian Protest—Canadia Application No. 2804298 dated Mar. 30, 2015, citing U.S. Pat. No. 3,133,309.
Chang-Seop Oh, "Recent Prospect of Polyurethanes", ReSEAT Analysis Report, Sep. 10, 2004, pp. 1-7, KR.
Chinese Office Action for corresponding Chinese Patent Application No. 201280002267.3 dated Mar. 30, 2016.
Chinese Office Action—Chinese Application No. 201280002267.3 dated Dec. 3, 2014, citing previously filed references CN101977587 and JP4588357.
Chinese Office Action—Chinese Application No. 201280002267.3 dated Mar. 18, 2014, citing previously filed references CN101977587 and US20090047495.
Chinese Office Action—Chinese Application No. 201280002267.3 dated Sep. 8, 2015.
Chinese Patent Invalidation Request for corresponding Chinese Patent Application No. 201280002267.3.
European Office Action for corresponding European Patent Application No. 12759918.1 dated Mar. 1, 2016.
European Office Action—European Application No. 12759918.1 dated Aug. 11, 2015.
European Office Action—European Application No. 12759918.1 dated Jun. 18, 2015, citing U.S. Pat. No. 3,133,309.
European Office Action—European Application No. 12759918.1 dated Oct. 12, 2014.
European Search Report—EP Application No. 12759918.1 dated Jan. 22, 2014 from European Patent Office.
Extract from pp. 22-23 of Korean Patent Court Ruling (case No. 2016heo8667), 1 page.
Foaming Plant, Copyrights 2006, pp. 1-7, Retrieved from the Internet Jun. 25, 2018<URL:http://www.foamtecintl.com/index.php?shpage=vpage&vpage=fpprofile&lang=en&plan=FP>.

(56) References Cited

OTHER PUBLICATIONS

George Woods, "Flexible Polyurethane Foams", Chemistry and Technology, 1982, pp. 94-95, Applied Science Publishers Ltd., Essex, England.
Indian Office Action—Indian Application No. 10805/CHENP/2012 dated Jul. 14, 2017, citing references listed within.
INOAC—Reticulated PU Foam, Posted: Nov. 2009, p. 1, Retrieved from the Internet Sep. 2, 2015, <URL: http://www.inostech.com/>.
International Search Report for International Application No. PCT/KR2012/002141 dated Oct. 31, 2012.
Japanes Office Action—Japan Application No. 2014-008657 dated Jun. 18, 2015.
Japanese Office Action for corresponding Japanese Patent Application No. 2014-008657 dated Mar. 9, 2017, citing previously filed reference.
Japanese Office Action for corresponding Japanese Patent Application No. 2014-008657 dated May 31, 2016, citing previously filed reference.
Japanese Office Action—Japan Application No. 2014-008657 dated Sep. 11, 2015.
Jong-Rae Park, "Catalytic Glycolysis of Polyether Urethane Foam Waste", Master's Thesis, Chonnam National University Graduate School, Department of Chemical Engineering, Aug. 1999, pp. 4-5, KR.
Korean Office Action with English Translation for Application No. 10-2011-0026466 dated Dec. 16, 2012.
Korean Office Action with English Translation for Application No. 10-2011-0026466 dated Jun. 6, 2012.
Malaysian Examination Report—Application No. PI2013000328 dated Apr. 3, 2015, citing previous filed references.
Notice of Allowance with English Translation for Application No. 10-2011-0026466 dated Apr. 17, 2013.
Notice of Opposition for EP 12759918.1 from European Patent Office dated Jul. 19, 2018, citing the above references.
Open Cell Foam, The Foam Factory, Retrieved from the Internet Nov. 11, 2016, pp. 1-2, <URL: http://www.thefoamfactory.com/opencellfoam/filter.html>.
Polyurethane Foam, p. 1, <URL: http://web.archive.org/web/20090220164156/http://casefoam.com/Polyurethane-foam.htm>.
Polyurethane Foam, Retrieved from the Internet Nov. 15, 2016, pp. 1-2, <URL: https://web.archive.org/web/20021223120233/http://www.casefoam.com/Polyurethanefoam.htm>.
Yoo, "Koean BB/CC Cushion Foundation Review", Aug. 16, 2013; http://www.liahyoo.com/2013/08/koran-bbcc-cushion-foundation.html.
Linde Group, "Plyurethane foaming", available online May 27, 2016.
Google date for Linde Group, "Polyurethane foaming", printed 2015.
TBK, "44 mm round tin pans", udated Aug. 2011: http://www.tkbtrading.com/item.php?item_id+1298&page=3.
Yang Xiao-hua, et al., "The preparation, properties and determinating of structure for open cell polyurethane foam", Journal of the Hebei Academy of Sciences, vol. 24, No. 3, pp. 59-61, Sep. 2007.

| POLYESTER-BASED URETHANE FOAM 1 (CONVENTIONAL URETHANE FOAM) | POLYESTER-BASED URETHANE FOAM 2 (Q100UT) | POLYESTER-BASED URETHANE FOAM 3 (QS100EB) |
|---|---|---|
|  |  |  |

↑ membranes of each pore is reticulated
Reticulation*

URETHANE FOAM FOR USE IN IMPREGNATING COSMETIC COMPOSITION

CROSS-REFERENCE TO RELATED APPLICATIONS

The present application is a continuation of U.S. application Ser. No. 14/034,650, filed Sep. 24, 2013, which is a continuation-in-part of PCT/KR2012/002141, which was filed Mar. 23, 2012 and designates the United States, which claims priority benefit of Korean Appl. No. KR10-2011-0026466, filed Mar. 24, 2011, the disclosures of all of which are incorporated herein by reference in their entireties. The present application is also a continuation of U.S. application Ser. No. 16/221,583, filed Dec. 17, 2018, which is a continuation-in-part of U.S. application Ser. No. 14/034,650, filed Sep. 24, 2013, which is a continuation-in-part of PCT/KR2012/002141, which was filed Mar. 23, 2012 and designates the United States, which claims priority benefit of Korean Appl. No. KR10-2011-0026466, filed Mar. 24, 2011, the disclosures of all of which are incorporated herein by reference in their entireties.

FIELD

This disclosure relates to urethane foam for use in impregnating cosmetic composition and a cosmetic including urethane foam.

BACKGROUND

In the old days, cosmetic compositions were used mainly indoors. However, as leisure activities have been generalized recently and modern life styles have been changed correspondingly, cosmetic compositions have been frequently used outdoors. Particularly, in the old days, UV protecting cosmetic compositions were used mostly in summer seasons. However, as modern people enjoy outdoor activities and recognize hazard of UV rays more and more, there is a tendency for UV protecting cosmetic compositions to be used frequently throughout all the seasons besides summer seasons. Therefore, there is an increasing need for cosmetic compositions convenient to use and easy to carry.

Polyester-based urethane foam was developed accidentally by a German technical specialist in the late 1940's during which development of plastics was in the midst. Since such urethane foam is based on polyester, it is also called ester foam. Producing such urethane foam requires no advanced technology. Thus, polyester-based urethane foam has been produced generally and used in various industrial fields, particularly those requiring strong tensile force.

However, polyester-based urethane foam tends to be broken easily under a wet environment. In addition, it has a microcellular structure and low air permeability, and thus shows low cushiony feel, softness and flexibility. As a result, polyester-based urethane foam is not suitable for use in impregnating a cosmetic composition, particularly a liquid cosmetic composition. Under these circumstances, there is an imminent need for developing urethane foam suitable for use in impregnating a cosmetic composition.

Polyester-based urethane foam tends to be brittle under wet environment and has a small cell structure and low air permeability. Thus, polyester-based urethane foam shows low cushioning property, softness and flexibility, so that it is not suitable for impregnation with a cosmetic composition, particularly a liquid cosmetic composition. Therefore, there has been a need for developing urethane foam suitable for impregnation with a cosmetic composition.

SUMMARY OF THE INVENTION

This disclosure is directed to providing urethane foam for use in impregnating a cosmetic composition, the urethane foam being capable of maintaining high stability of the cosmetic composition to be impregnated therein and high post-impregnation stability.

In one general aspect, there is provided polyether-based urethane foam for use in impregnating a cosmetic composition, a cosmetic composition-impregnated polyether-based urethane foam, and a cosmetic including polyether-based urethane foam impregnated with a cosmetic composition. The polyether-based urethane foam disclosed herein maintains high stability even after it is impregnated with a cosmetic composition, shows high durability and excellent filling ability and dischargeability when it is impregnated with a cosmetic composition, and thus is suitable for impregnation with a cosmetic composition. The polyether-based urethane foam disclosed herein enhances the portability and feeling in use of a cosmetic composition.

The polyether-based urethane foam disclosed herein maintains high stability even after carrying out impregnation with a cosmetic composition, and improves portability and touch feel of a cosmetic composition.

DETAILED DESCRIPTION

Figure 1:
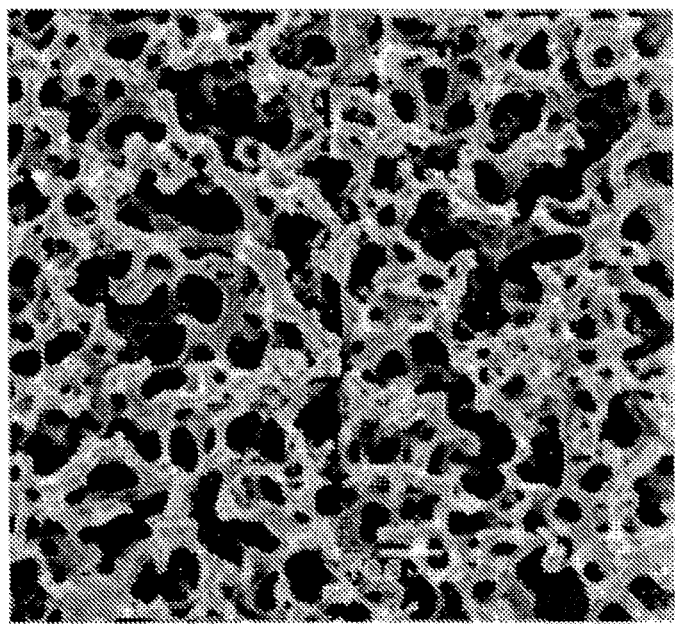
FIG. 1 is a microscopic view of wet polyether-based urethane foam.

In one aspect, there is provided polyether-based urethane foam for use in impregnating a cosmetic composition. In another aspect, the polyether-based urethane foam may function as a carrier in which a cosmetic composition is supported and retained.

As used herein, the term 'urethane foam' means a foamed and solidified polyurethane resin, and is also referred to as 'foamed urethane'.

As used herein, "durability" means a degree of any material to maintain as it is without melting, tearing or swelling when the material is impregnated with a cosmetic composition and stored at a predetermined temperature for a predetermined time. As used herein, "filling ability" means ability of any material to fill a cosmetic composition therein, and may be represented as time required for filling a predetermined amount of cosmetic composition. As used herein. "dischargeability" means an amount of cosmetic composition discharged when taking the cosmetic composition from any material impregnated therewith. When taking the cosmetic composition, the cosmetic composition is required to be discharged in an adequate amount, not too much, but not too little.

According to an embodiment, the urethane foam, particularly polyether-based urethane foam disclosed herein maintains high durability even after it is impregnated with a cosmetic composition, allows easy filling of a cosmetic composition, an discharges an adequate amount of cosmetic composition, as compared to other materials, including acrylonitrile-butadiene rubber (NBR), styrene-butadiene rubber (SBR), natural rubber (NR), PU-PE flocking, polyethylene (PE), ethylene vinyl acetate (EVA), polyolefin (PO) and polyvinyl alcohol (PVA). Thus, the urethane foam disclosed herein is suitable for impregnation with a cosmetic composition.

In one aspect, urethane foam, particularly polyether-based urethane foam is more resistant against humidity as compared to polyester-based urethane foam, and thus shows low brittleness and high stability even under a high-humidity condition and is not broken easily under a high-humidity condition and shows high stability. Particularly, polyether-based urethane foam shows higher durability after being impregnated with a cosmetic composition, as compared to polyester-based urethane foam, and thus is suitable for impregnation with a cosmetic composition. In addition, the polyether-based urethane foam has a larger cellular structure than polyester-based urethane foam, and thus has improved air permeability, cushiony feel/cushioning property, softness and flexibility. Further, the polyether-based urethane foam requires reduced cost for production, and thus has higher cost-efficiency than polyester-based urethane foam.

In one aspect, urethane foam may include dry urethane foam or wet urethane foam. Particularly, wet polyether-based urethane foam has the properties as shown in the following Table 1.

TABLE 1

| Item | |
|---|---|
| Pore size | 200 μm |
| Surface Properties | Hydrophilic |
| ASKER DUROMETER HARDNESS Type C hardness | 90 |
| Tensile strength | 15 kgf/cm$^2$ |
| Elongation | 260% |
| Apparent specific gravity (g/cm$^3$) | 0.21 |
| Moisture holding ratio | 420% |

In general, wet polyether-based urethane foam has a smaller pore size and more dense structure than dry polyether-based urethane foam. While dry polyether-based urethane foam has oleophilic surface properties, wet polyether-based urethane foam has hydrophilic surface properties as a result of wet foaming. Wet polyether-based urethane foam is continuous microporous urethane foam having uniform and high porosity, shows high water/oil absorbability, and produces no particles spontaneously. FIG. 1 is a microscopic view of wet polyether-based urethane foam.

In one aspect, urethane foam may have a quenched or reticulated structure. In another aspect, urethane foam may have a reticulated structure that allows uniform and easy impregnation with a cosmetic composition and provides a high impregnation ratio.

According to still another embodiment, the polyether-based urethane foam is impregnated with cosmetic composition, which is different as compared to a conventional cosmetic applicator (puff or cosmetic sponge). The cosmetic applicator is used when a user applies a cosmetic composition on a skin. Specifically, it is used when a cosmetic is applied to a skin in such a way to touch an applicator with a cosmetic composition on a skin. The cosmetic applicator itself does not contain any cosmetic composition, whereas the impregnation material for cosmetic composition impregnates and stores a cosmetic composition before a user actually uses it (durability and filling property are necessary). When the user actually uses it, a proper amount of cosmetic composition is applied to a cosmetic applicator (discharging property is necessary). The impregnation material for a cosmetic composition of the present invention does not directly contact with a skin, but contains a cosmetic composition, so a certain applicator is necessary. In case of a cosmetic applicator, specifically, a puff, when a cosmetic composition penetrates deep into the inner side of a sponge, the cosmetic composition is not easy to be applied to a user's skin when in use, so the cosmetics should not easily penetrate into the deep portion of the sponge. The cosmetic composition-impregnated foam according to the present invention itself is an impregnation material of a cosmetic composition which has an impregnation function, so it is definitely different from a cosmetic applicator (puff).

Figure 9:
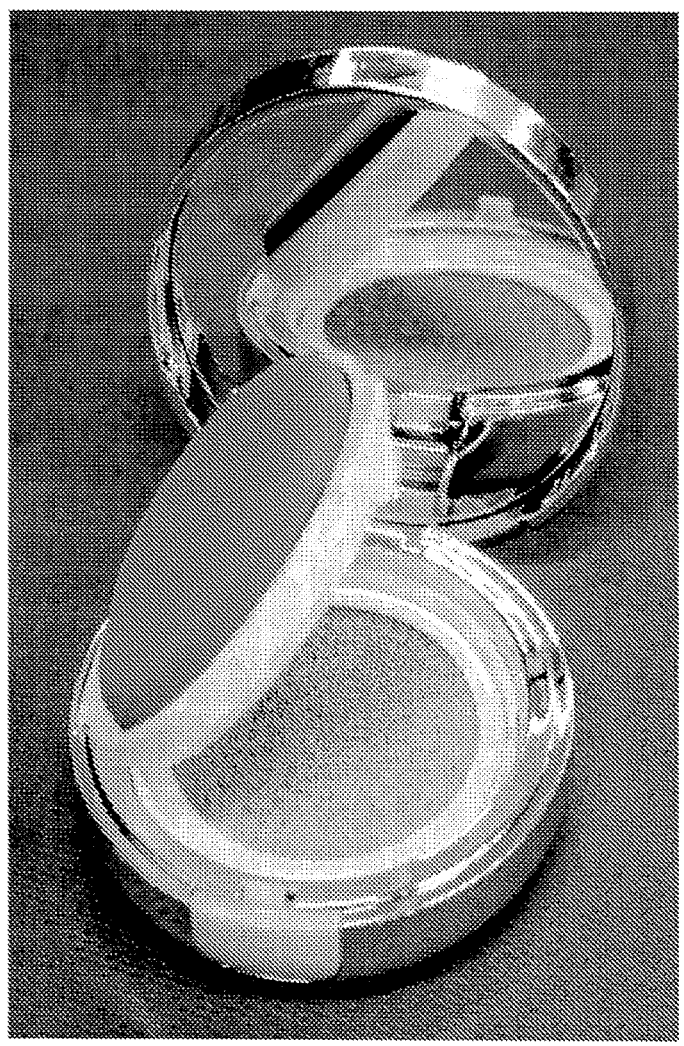
FIG. 9 shows a pact with a built-in urethane foam impregnated with a W/O type emulsified make-up cosmetic composition.

FIG. 9 is a view illustrating a product containing an impregnation material for a cosmetic composition with which a cosmetic composition of the present invention is impregnated.

According to still another embodiment, urethane form may have a reticulated structure. In the case of a reticulated structure, it is easy to carry out homogeneous impregnation of urethane foam with a cosmetic composition, thereby providing a higher impregnation ratio.

Figure 10:
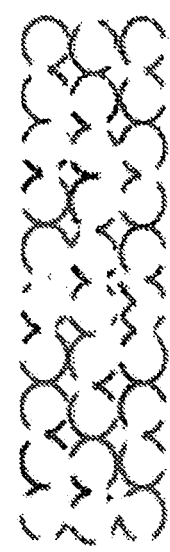
FIG. 10 is a 3D view illustrating a reticulated structure of a polyether-based urethane foam.
Figure 10:
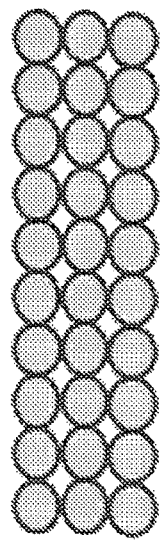

The reticulated structure urethane foam according to the present invention is formed by an additional process. The reticulated structure is also called a 3D network structure. The reticulated structure is made in a network shape as the balloon-shaped membranes (walls) are reticulated. The reticulated structure has features in that air can penetrate, and liquid can be absorbed and discharged. The "reticulation" is a kind of process for changing to a reticulated structure depending on its application after a foamed structure is made. In case of a sponge foam, the membranes of each pore is broken and reticulated. The reticulation process is shown in FIG. 10. The reticulated structure of the present invention is different from a conventional foamed structure in which cosmetic composition cannot penetrate deep into the inner side having a 3D membrane structure in a sponge. The present invention is also different from the top of the urethane foam support covered by cloth, net, non-woven fabric, etc.

According to still another embodiment, urethane foam may have an open cell structure.

The urethane foam made through a foaming and concreting process has a closed cell or semi-open cell structure. When urethane foam has a closed cell structure, air bubbles may be trapped in urethane so that the urethane foam may not be impregnated with a low-viscosity emulsified cosmetic composition easily. The present invention can provide a complete open cell structure in which only frames remain after the cell surfaces of the foams are reticulated through the reticulation process.

In one aspect, urethane foam may have a density of 1 to 3 pounds per cubic feet (pcf), particularly 1 to 2 pcf. When urethane foam has a density less than 1 pcf, a cosmetic composition may be liberated excessively and thus is not convenient to use. When urethane foam has a density higher than 3 pcf, it is not possible to provide a sufficient number of pores through which a cosmetic composition is impregnated, thereby making it difficult to impregnate a cosmetic composition effectively.

Herein, density may be determined, for example, based on ASTM D3547.

In one aspect, urethane foam may have a pore number of 70 to 120 pores per inch (ppi), particularly 75 to 95 ppi. When urethane foam has a pore number less than 70 ppi, it has low elasticity, provides no comfort in use and has difficulty controlling the flowability of a cosmetic composition. When urethane foam has a pore number greater than 120 ppi, it provides low durability and poor touch feel of a cosmetic composition during use.

As used herein, 'ppi' (pore per inch) is a unit expressing the size of a pore, and refers to the number of pores per inch, i.e., pore number shown on a 1-inch line in the section of a foam material. As a ppi number increases, pore size decreases. Since such a pore number is determined by visual inspection, recognition of pores depends on condition of pores, approved in different manners by different countries. For example, Visual Counting Methods (ppi check) of Japan, USA and Europe are shown in the following Table 2.

TABLE 2

Visual Counting Methods (ppi check)

| Determination of ppi | Japan | USA | Europe |
|---|---|---|---|
| Method | Count only full cells (completely shaped cells) corresponding to the designated line as observed by a microscope | Count full cells (completely shaped cells within the designated line and on the boundary) observed by a microscope; 1.8 times of the value determined Japan | Count all cells (all cells observed within the designated line and on the boundary, regardless of cell shapes) observed by a microscope; 2 in times of the value determined in Japan |

Herein, Visual Counting Method of USA is used to determine ppi. Therefore, the ppi of urethane foam according to an aspect is different by about 30 ppi from the ppi thereof determined by using Visual Counting Method of Japan.

The cell size of the present invention is an average value measured using an optical microscope (NIKON ECLIPSE 80i).

In one aspect, urethane foam before a cosmetic composition is impregnated may have an ASKER hardness of 10 to 70, particularly 20 to 60, particularly 35-55, and more particularly 30 to 50 as measured by DUROMETER HARDNESS TESTER (Type F) available from ASKER. When urethane has a hardness less than 10 and is too soft, a cosmetic composition impregnated in the urethane foam may be discharged in an excessively large amount, when taking it with cosmetic tools/utensils used for a make-up composition enclosed in a packed container, for example by nitrile butadiene rubber (NBR) puff, or hands. When urethane foam has a hardness larger than 70 and is too hard, it is difficult to discharge a cosmetic composition from the urethane foam.

In one aspect, urethane foam may have an open cell structure. When urethane foam has a closed cell structure, air bubbles are kept in urethane so that a low-viscosity emulsion type cosmetic composition may not be impregnated therein easily. Thus, urethane foam having an open cell structure may be used specifically.

In one aspect, the cosmetic composition to be impregnated in urethane foam includes a liquid cosmetic composition, particularly an emulsion type cosmetic composition, and more particularly a water in oil (W/O) type or oil in water (O/W) type emulsion cosmetic composition.

According to an embodiment, the cosmetic composition applicable to the urethane foam for impregnation may be a liquid cosmetic composition, particularly an emulsified cosmetic composition, and more particularly a water in oil (W/O) type or oil in water (O/W) type emulsified cosmetic composition.

In one aspect, the emulsion cosmetic composition may have a low viscosity, particularly of 5,000 to 15,000 centipoise (cps), and more particularly of 6,000 to 10,000 cps. When the emulsion cosmetic composition has a viscosity less than 5,000 cps, oil phase/aqueous phase separation occurs right after preparing the emulsified cosmetic composition. As a result, it is difficult to impregnate urethane foam with such a composition. When an emulsified cosmetic composition has a viscosity higher than 15,000 cps, it provides an undesirable tacky and heavy touch feel during skin application.

According to still another embodiment, the viscosity may be determined by a viscometer. The measured values may include LVDV II+PRO or RVDV III ULTRA, spindle No. 63 or spindle No. 64, speed RPM or 12 RM, the values of which are not limited thereto. The viscosity value may vary with systems used for measurement, spindle number, rpm, or the like.

In one aspect, the cosmetic composition includes both a skin care composition and a make-up composition. Particular non-limiting examples of the cosmetic composition may include make-up primer, make-up base, foundation, powder, twin cake, lipstick, lip gloss, eye shadow, eyebrow, concealer, lip liner, blusher, UV protecting agent/UVprotector, lotion, cream or essence. More particularly, the cosmetic composition may be formulated into make-up primer, make-up base, liquid or solid foundation, powder, twin cake, lipstick, lip gloss, eye shadow, eyebrow, concealer or blusher, but is not limited thereto.

Figure 2:
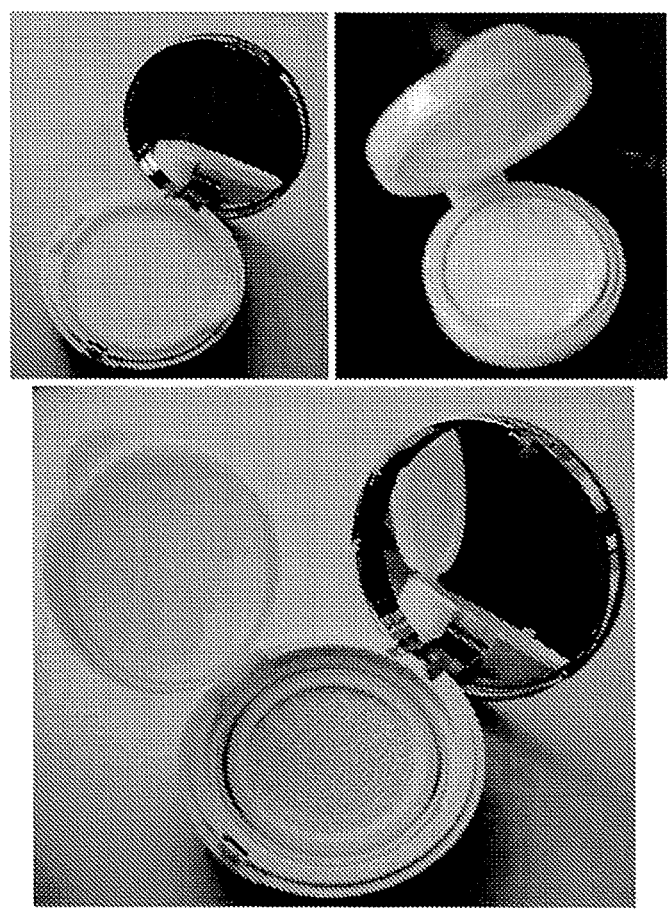
FIG. 2 shows a packed make-up product in which a urethane foam impregnated with a W/O type emulsion make-up composition is enclosed.

In one aspect, there is provided a cosmetic product in which polyether-based urethane foam impregnated with a cosmetic composition is enclosed. The cosmetic product includes a cosmetic composition applied to the polyether-based urethane foam disclosed herein, and thus allows high-quality packing of the cosmetic composition. Therefore, the cosmetic allows good packing of a cosmetic composition, supports a cosmetic composition homogeneously for a long time, enables an adequate amount of cosmetic composition to be discharged therefrom when taking the cosmetic composition, and maintains high durability and stability for a long time. In still another aspect, the cosmetic may be provided as a cosmetic container generally called 'pact' in brief and including a container that has a bottom portion in which the polyether-based urethane foam is received, and a top portion as a lid to which a mirror or the like may be attached. Such polyether-based urethane foam provided in a pact container is shown in FIG. 2.

The examples, comparative examples, preparation examples and test examples will now be described to describe the construction and effects of the present disclosure in more detail. The following examples, comparative examples, preparation examples and test examples are for illustrative purposes only and not intended to limit the scope of the present disclosure.

[Test Example 1] Investigation of Characteristics of Materials

Figure 3:
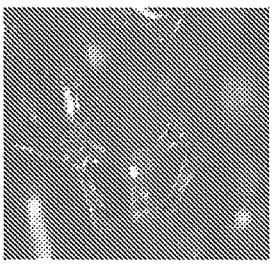
FIG. 3 is a microscopic view of the urethane foams listed in Table 2, each magnified at 10×0.3.
Figure 3:
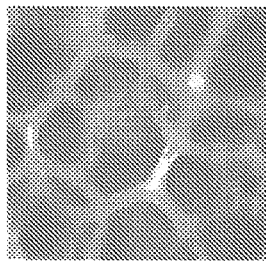
Figure 3:
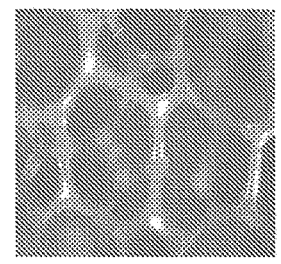
Figure 4:
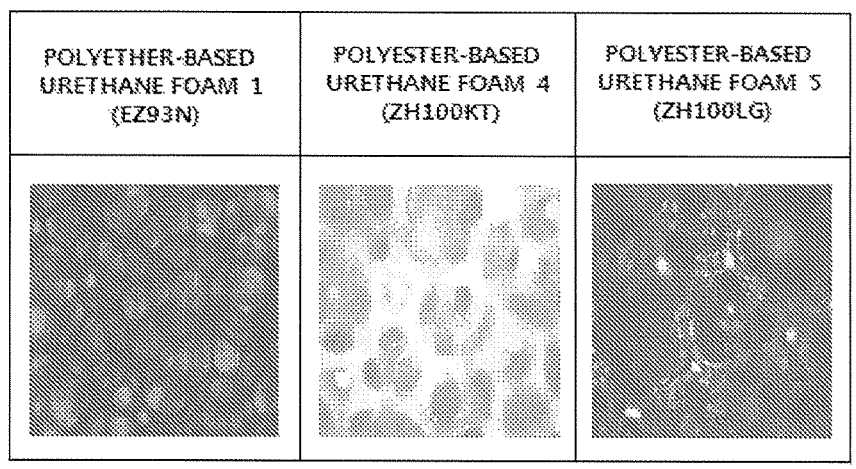
FIG. 4 is a microscopic view of the urethane foams listed in Table 3, each magnified at 10×0.3.

To select urethane foam suitable for impregnation with a W/O type or O/W type low-viscosity emulsion cosmetic composition, various types of urethane foam are determined for their properties. The following Tables 3 and 4 show each type of urethane foam and the corresponding properties. In addition, FIG. 3 and FIG. 4 are microscopic views of each type of urethane foam magnified at 10×0.3.

TABLE 3

|  | Polyester-based urethane foam 1 (conventional urethane foam) | Polyester-based urethane foam 2 (Q100UT) | Polyester-based urethane foam 3 (QS100EB) |
|---|---|---|---|
| Pore per inch (ppi) | 80 ppi | 85 ppi | 85 ppi |
| Density (pcf) |  | 1.7 | 1.7-2.0 |
| Available from | Germany | Foamtec(Thailand) | Foamtec(Thailand) |
| Remarks | Flexible polyurethane foam | Polyester-Polyurethane, Quenched foam | Polyester-Polyurethane, Reticulated foam |
| Hardness | 45 | 48 |  |

TABLE 4

|  | Polyether-based urethane foam 1 (EZ93N) | Polyester-based urethane foam 4 (ZH100KT) | Polyester-based urethane foam 5 (ZH100LG) |
|---|---|---|---|
| Pore per inch (ppi) | 88-100 ppi | 90 ppi | 90 ppi |
| Density (pcf) | 1.8-2.0 | 5.4-6.60 | 5.4-6.60 |
| Available from | Foamtec (Thailand) | Foamtec (Thailand) | Foamtec (Thailand) |
| Remarks | Polyether-Polyurethane, Reticulated foam | Polyester-Polyurethane, Reticulated foam | Polyester-Polyurethane, Reticulated foam |
| Hardness | 45 |  |  |

In Table 4, Polyether-based urethane foam 1 is dry polyether-based urethane foam.

To select a material suitable for impregnation of a cosmetic composition, the following ten types of materials are provided: acrylonitrile-butadiene rubber (NBR), styrene-butadiene rubber (SBR), natural rubber (NR), polyether-based urethane (PU-ether), polyester-based urethane (PU-ester), PU-PE flocking (flocking), polyethylene (PE), ethylene vinyl acetate (EVA), polyolefin (PO) and polyvinyl alcohol (PVA). Each material has the characteristics as shown in the following Tables 5 and 6.

TABLE 5

|  | NBR | SBR | NR | PU-ether | PU-ester |
|---|---|---|---|---|---|
| Characteristics | Controllable pore size, elastic | Controllable pore size, soft and elastic | Controllable pore size, soft and elastic | Variable pore size | Variable pore size |
| Pore size | 70-100 ppi | 70-100 ppi | 70-100 ppi | 88-100 ppi | 88-100 ppi |

TABLE 6

|  | flocking | PE | EVA | PO | PVA |
|---|---|---|---|---|---|
| Characteristics | Used for cosmetic puff | Moisture-resistant, highly heat insulating | Light and soft | Open cell structure, soft | Uniform and continuous open cell structure, excellent water-retaining, water-absorbing and dust-absorbing properties |
| Pore size | 70-90 ppi | 80-100 ppi | 80-100 ppi | 90-110 ppi | 70-100 ppi |

[Test Example 2] Evaluation of Formulation Stability

Figure 5:
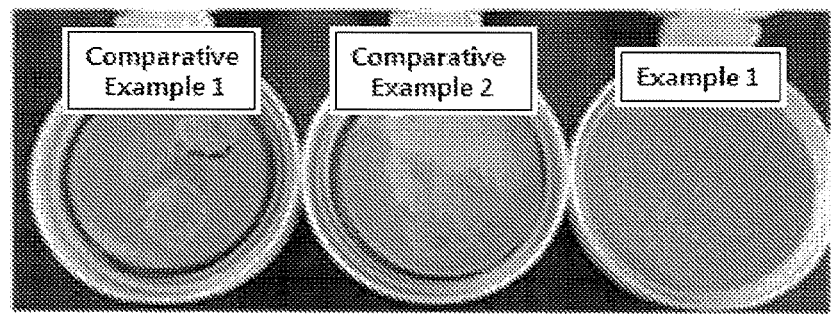
FIG. 5 shows photographs of Example 1, Comparative Example 1 and Comparative Example 2 after storing them at 50° C. for 2 hours.
Figure 6A:
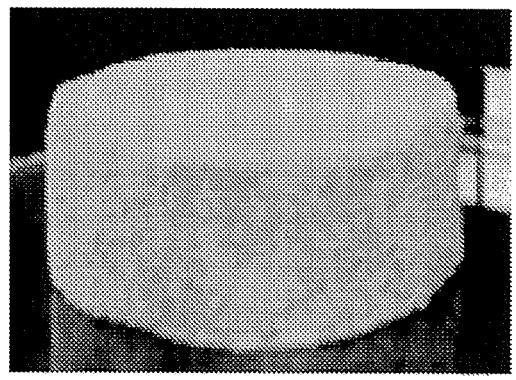
FIGS. 6A-6J show ten types of materials each of which is impregnated with 15 g of a cosmetic composition and then stored at 55° C. for 7 days (6A: NBR, 6B: SBR, 6C: NR, 6D: PU-ether, 6E: PU-ester, 6F: flocking, 6G: PE, 6H: EVA, 6I: PO, 6J: PVA)
Figure 6B:
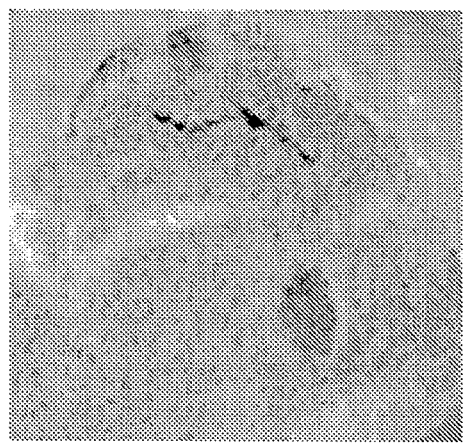
Figure 6C:
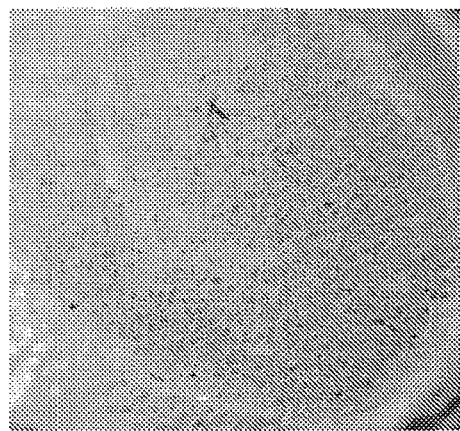
Figure 6D:
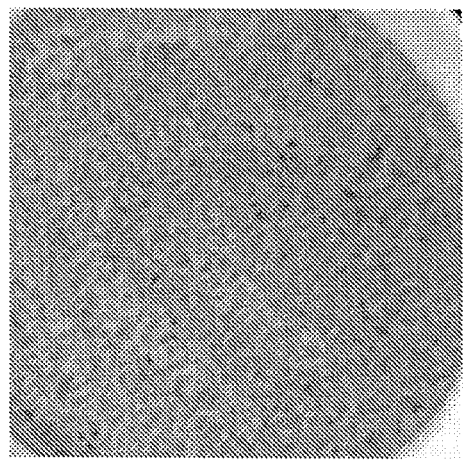
Figure 6E:
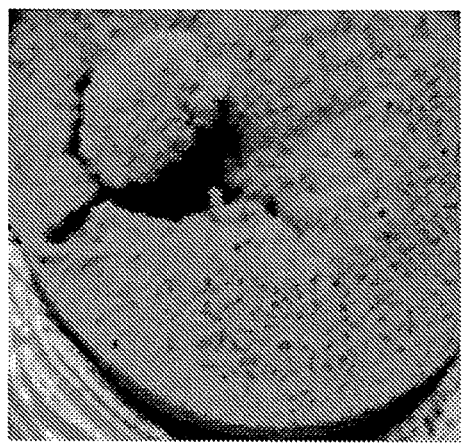
Figure 6F:
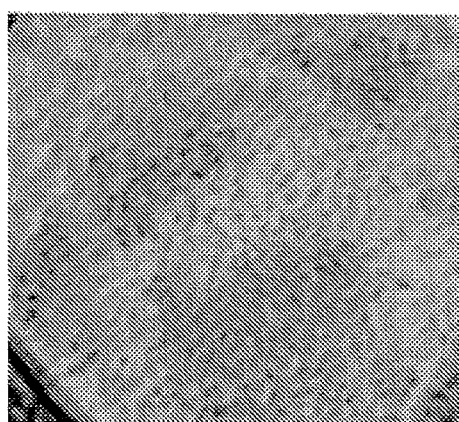
Figure 6G:
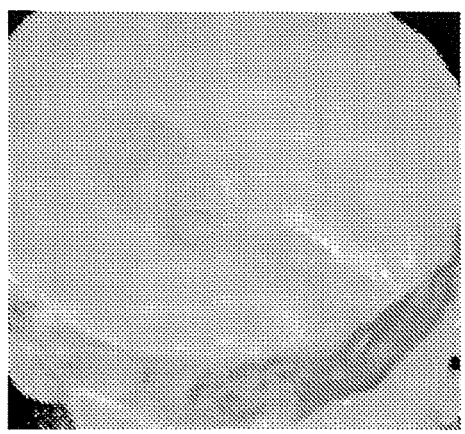
Figure 6H:
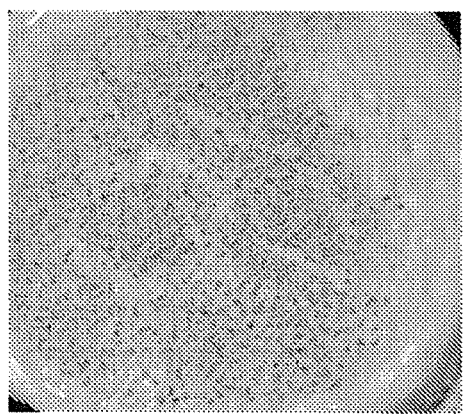
Figure 6I:
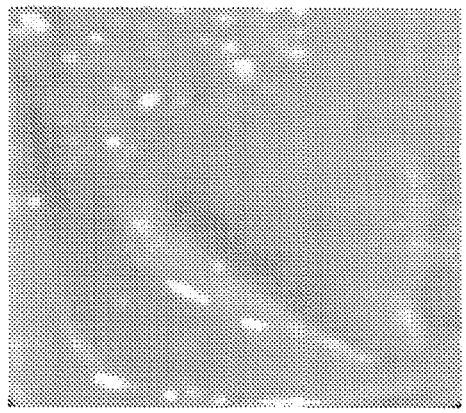
Figure 6J:
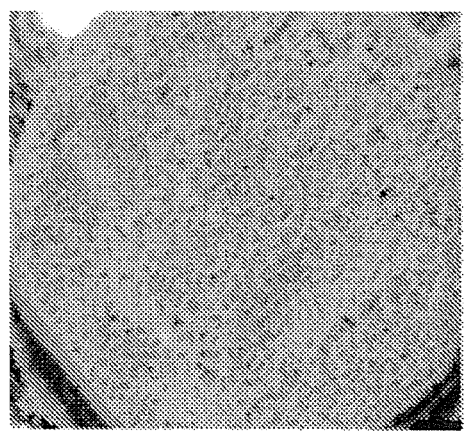

Among the different kinds of urethane foam listed in Tables 3 and 4, Polyether-based urethane foam 1 (Example 1), Polyester-based urethane foam 2 (Comparative Example 1) and Polyester-based urethane foam 3 (Comparative Example 2) are selected and subjected to impregnation with a W/O type emulsion make-up composition. Then, their stabilities are evaluated as a function of storage temperature and time. The results are shown in the following Table 7 and FIG. 5. FIG. 5 shows photographs of Example 1, Comparative Example 1 and Comparative Example 2 after storing them at 50° C. for 2 hours.

TABLE 7

|  | 55° C., after 7 days | 45° C.→30° C.→frozen at -10° C. (each for 8 hours), after 5 days | 30° C., after 7 days |
|---|---|---|---|
| Example 1 | Stable | Stable | Stable |
| Comparative Example 1 | Urethane foam broken | Urethane foam broken | Stable |
| Comparative Example 2 | Urethane foam broken | Urethane foam broken | Stable |

As can be seen from the above results, when each foam is impregnated with a W/O type emulsion make-up composition, each urethane foam according to Comparative Examples 1 and 2 is broken, causes separation of the make-up composition and generates air bubbles with time under a high temperature or severe change in temperature, and thus is shown to be very unstable. On the contrary, Example 1 substantially maintains its original state and shows high stability.

Therefore, it can be seen that polyether-urethane foam shows higher stability than polyester-based urethane foam upon impregnation with a cosmetic composition, and thus is more suitable for impregnating a cosmetic composition.

The ten types of materials as described in Test Example 1 are selected and classified into two groups having a similar pore size, and are evaluated for durability. The test method will be described in detail hereinafter.

Each material is formed into a circular shape having a size of diameter 48 mm×thickness 10 mm, and is impregnated with 15 g of the same cosmetic composition having a viscosity of 10,000 cps. Then, each material is stored at 55° C. for 7 days and checked for its condition. The results are shown in the following Tables 8 and 9.

TABLE 8

| NBR | SBR | NR | PU-ether | PU-ester |
|---|---|---|---|---|
| Inappropriate, swelled with cosmetic composition | Easily torn when pressed with finger | Easily torn when pressed with finger | Appropriate, maintaining shape and volume | Melted, cracked when pressed with finger |

TABLE 9

| flocking | PE | EVA | PO | PVA |
|---|---|---|---|---|
| Melted, stuck on bottom of container | Good, maintaining shape and volume | Good, maintaining shape and volume | Melted, stuck on bottom of container | Good, maintaining shape and volume |

FIGS. 6A-6J show each of the materials after each is impregnated with a cosmetic composition and stored for 7 days (6A: NBR, 6B: SBR, 6C: NR, 6D: PU-ether, 6E: PU-ester, 6F: flocking, 6G: PE, 6H: EVA, 6I: PO, 6J: PVA).

As can be seen from FIGS. 6A-6J, polyether-based urethane foam maintains its shape and volume even after being impregnated with a cosmetic composition, and thus shows the highest durability.

[Test Example 3] Evaluation of Filling Ability

Figure 7:
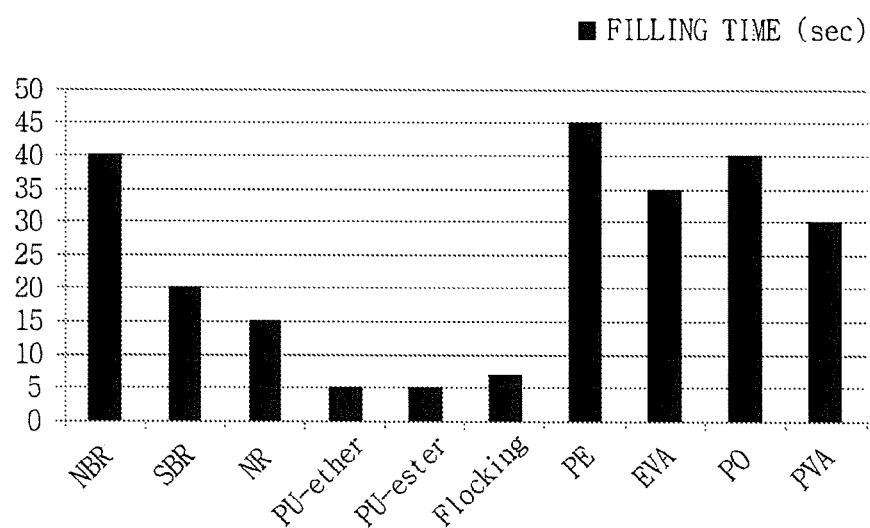
FIG. 7 is a graph illustrating the time required for impregnation of 15 g of the same cosmetic composition in each of the ten types of materials.

The ten types of materials as described in Test Example 1 are selected and classified into two groups having a similar pore size, and are evaluated for filling ability. Particularly, each material is formed into a circular shape having a size of diameter 48 mm×thickness 10 mm. Then, measured is the time required for each material to be impregnated with 15 g of the same cosmetic composition having a viscosity of 10,000 cps. The results are shown in the following Table 10 and FIG. 7.

TABLE 10

|  | Filling time (sec) |
|---|---|
| NBR | 40 |
| SBR | 20 |
| NR | 15 |
| PU-ether | 5 |
| PU-ester | 5 |
| flocking | 7 |
| PE | 45 |
| EVA | 35 |
| PO | 40 |
| PVA | 30 |

As can be seen from the above results, polyether-based urethane foam and polyester-based urethane foam have the smallest filling time. This suggests that polyether-based urethane foam and polyester-based urethane foam have the highest cosmetic composition filling ability.

[Test Example 4] Evaluation of Dischargeability (1) Investigation of Optimum Discharge Amount First, to investigate the amount of a cosmetic composition suitable as a unit discharge amount, 50 persons are allowed to apply different amounts of cosmetic composition and to evaluate each of the following items from which the optimum amount may be derived by rating it as grade 1 to grade 9 (higher grade represents better quality). The results are shown in the following Table 11. "Applicability" refers to a degree of goodness of skin application amount, "cosmetic effect" refers whether or not the cosmetic composition shows excellent coverage on skin without agglomeration and allows uniform make-up within an adequate time, "comfort" refers to a degree of comfort in use of cosmetic composition without take-up many times while allowing easy control of application amount, and 'satisfaction" refers to a degree of overall satisfaction.

TABLE 11

| Unit application amount (g) | Applicability | Cosmetic effect | Comfort | Satisfaction |
|---|---|---|---|---|
| 0.05 | 1 | 1 | 1 | 1 |
| 0.1 | 1 | 1 | 1 | 1 |
| 0.3 | 7 | 5 | 5 | 5 |
| 0.5 | 9 | 9 | 9 | 9 |
| 0.7 | 5 | 5 | 3 | 3 |
| 0.9 | 1 | 3 | 1 | 1 |
| 1.1 | 1 | 1 | 1 | 1 |
| 1.3 | 1 | 1 | 1 | 1 |
| 1.5 | 1 | 1 | 1 | 1 |

As can be seen from the above results, when the unit application amount of a cosmetic composition is 0.3-0.5 g, particularly is about 0.5 g, a high cosmetic effect, comfort and satisfaction are obtained. Therefore, it can be seen that when a cosmetic composition is taken once, 0.3-0.5 g, particularly about 0.5 g is adequate as a unit application amount.

(2) Evaluation of Dischargeability

Figure 8:
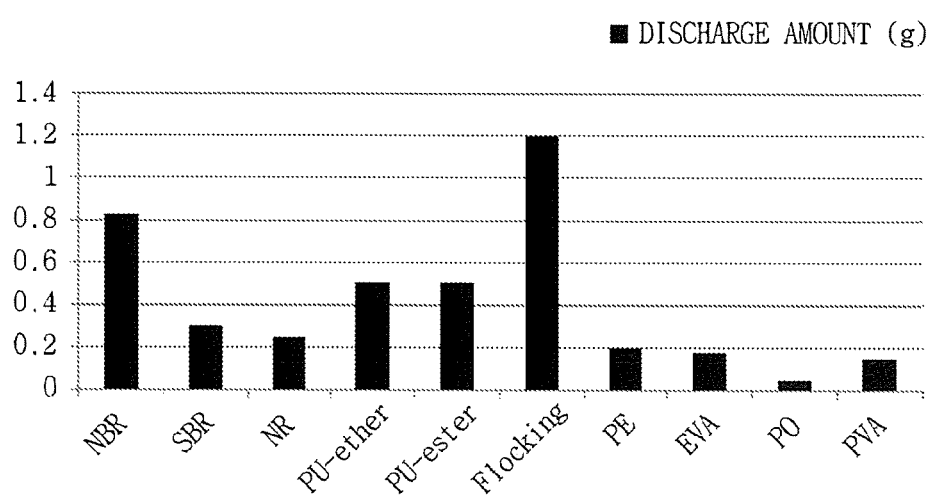
FIG. 8 is a graph illustrating the amount (g) of cosmetic composition discharged when taking the cosmetic composition from each of the ten types of materials impregnated with the same cosmetic composition.

The ten types of materials as described in Test Example 1 are selected and classified into two groups having a similar pore size, and are evaluated for dischargeability. Particularly, each material is impregnated with 15 g of the same cosmetic composition having a viscosity of 10,000 cps, and the amount (g) of cosmetic composition discharged when taking the cosmetic composition once by using puff. In addition, 50 persons are allowed to apply a cosmetic composition by using the ten types of materials, and to evaluate each of applicability, cosmetic effect, comfort and satisfaction by rating it as grade 1 to grade 9 (higher grade represents better quality). The results are shown in the following Table 12 and FIG. 8.

TABLE 12

|  | Discharge amount (g) | Applicability (grade) | Cosmetic effect (grade) | Comfort (grade) | Satisfaction (grade) |
|---|---|---|---|---|---|
| NBR | 0.83 | 1 | 3 | 1 | 1 |
| SBR | 0.3 | 5 | 7 | 5 | 5 |
| NR | 0.25 | 3 | 7 | 3 | 3 |
| PU-ether | 0.5 | 9 | 9 | 9 | 9 |
| PU-ester | 0.5 | 9 | 9 | 9 | 9 |
| Flocking | 1.2 | 1 | 1 | 1 | 9 |
| PE | 0.2 | 3 | 5 | 3 | 3 |
| EVA | 0.18 | 3 | 3 | 1 | 3 |
| PO | 0.05 | 1 | 1 | 1 | 1 |
| PVA | 0.15 | 1 | 1 | 1 | 1 |

[Preparation Examples 1 and 2] Preparation of UV Protecting Cosmetic Composition In Preparation Examples 1 and 2, W/O type emulsion UV protecting cosmetic compositions are prepared according to the formulation of the following Table 13.

Particularly, a UV protecting agent is introduced to oily ingredients and dissolved and emulsified therein. Next, the oily ingredients are mixed with a surfactant and heated to and agitated at 80° C. so that the mixture is homogenized. Then, a pigment is further added thereto, followed by agitation and homogenization, to provide an oily part. In a separate mixer, aqueous ingredients are mixed and heated to and agitated at 80° C. to provide a completely dissolved aqueous part. The prepared aqueous part is introduced gradually to the oily part and subjected to emulsification by using a homogenizer mixer. After cooling to 50° C., skin protecting ingredients and fragrances are introduced thereto, followed by cooling, to provide a low-viscosity W/O type emulsion UV protecting cosmetic composition.

TABLE 13

| | | Ingredients (wt %) | Prep. Ex. 1 | Prep. Ex. 2 |
|---|---|---|---|---|
| Oily Part | Oily Ingredients | Ozokerite | 0.1 | 1.0 |
| | | Dicaprylyl carbonate | 10.00 | 10.00 |
| | Preservative | Methyl paraben | 0.100 | 0.100 |
| | UV protecting agents | Octylmethoxy cinnamate | 7.000 | 7.000 |
| | | Isoamyl p-methoxy cinnamate | 2.000 | 2.000 |
| | Pigment | Disteardimonium hectorite | 0.20 | 1.50 |
| | Oily Ingredients | Decamethylcyclopentasilxane | 16.00 | 16.00 |
| | Emulsifiers | Sorbitan sesquioleate | 2.000 | 2.000 |
| | | Lauryl PEG/PPG-18/18 methicon | 1.500 | 1.500 |
| | Pigments | Polymethyl methacrylate | 5.00 | 5.00 |
| | | Titanium dioxide/Aluminum hydroxide/Stearic acid | 7.00 | 7.00 |
| Aq. Part | | Water | To 100 | To 100 |
| | Moisturizer | Glycerin | 8.000 | 8.000 |
| | Emulsion stabilizer | Sodium chloride | 1.00 | 1.00 |
| | | Fragrance | 0.400 | 0.400 |
| | | Total | 100 | 100 |

In Table 13, disteardimonium hectorite functions as a thickening agent, polymethyl methacrylate serves as a pure body pigment, and titanium dioxide/aluminum hydroxide/stearic acid serves as an inorganic UV protecting agent.

[Test Example 3] Evaluation of Preference Depending on Hardness of Urethane Foam Different types of polyether-based urethane foam having a different value of hardness are impregnated with Preparation Examples 1 and 2, and user preference of each case is determined. Particularly, 50 females are divided into two groups (each group having 25 persons). They are allowed to apply each of Preparation Example 1 and Preparation Example 2 impregnated in polyether-based urethane foam having a different value of hardness to their skin with NBR puff for 2 days. Then, overall user preference including touch feel and coating quality is evaluated in each case. The results are shown in the following Tables 14 and 15.

TABLE 14

| | Cosmetic composition used for impregnation | Hardness of urethane foam (ASKER hardness, Type F) | Preference (%) |
|---|---|---|---|
| Example 2 | Preparation Example 1 | 5 | 5 |
| Example 3 | Preparation Example 1 | 80 | 10 |
| Example 4 | Preparation Example 1 | 40 | 85 |

TABLE 15

| | Cosmetic composition used for impregnation | Hardness of urethane foam (ASKER hardness, Type F) | Preference (%) |
|---|---|---|---|
| Example 5 | Preparation Example 2 | 5 | 5 |
| Example 6 | Preparation Example 2 | 80 | 5 |
| Example 7 | Preparation Example 2 | 40 | 90 |

As can be seen from the above results, the highest preference is available when polyether-based urethane foam used for impregnation with both compositions according to Preparation Examples 1 and 2 has Asker hardness value of 40.

As can be seen from the above results, polyether-based urethane foam and polyester-based urethane foam show the most adequate discharge amount. In addition, polyether-based urethane foam and polyester-based urethane foam provide excellent applicability, cosmetic effect, comfort and satisfaction. This means that polyether-based urethane foam and polyester-based urethane foam shows the highest cosmetic composition dischargeability.

As can be seen from the foregoing, polyether-based urethane foam having excellent durability, filling ability and dischargeability of a cosmetic composition is suitable for use in impregnation with a cosmetic composition.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A cosmetic product comprising:
an emulsified cosmetic composition;
a polyether-based urethane foam impregnated with the emulsified cosmetic composition; and
a container in which the polyether-based urethane foam impregnated with the emulsified cosmetic composition is stored,
wherein the emulsified cosmetic composition is released from the polyether-based urethane foam impregnated with the emulsified cosmetic composition to a cosmetic tool that is separate from the polyether-based urethane foam and that tool is for applying the released emulsified cosmetic composition to skin, and
wherein the polyether-based urethane foam has a pore number of 70 to 120 pores per inch (ppi) before the emulsified cosmetic composition is impregnated, and
wherein the polyether-based urethane foam has a reticulated structure and a density of 1-3 pounds per cubic foot (pcf) as determined by ASTM D3547 before the emulsified cosmetic composition is impregnated.

2. The cosmetic product of claim 1, wherein the polyether-based urethane foam has a hardness of 10-70 as determined by a durometer before the cosmetic composition is impregnated.

3. The cosmetic product of claim 1, wherein the emulsified cosmetic composition is a water in oil (W/O) composition or an oil in water (O/W) composition.

4. The cosmetic product of claim 1, wherein the emulsified cosmetic composition has a viscosity of 5,000-15,000 cps.

5. The cosmetic product of claim 1, wherein the emulsified cosmetic composition is a UV-protecting cosmetic composition.

6. The cosmetic product of claim 1, wherein the cosmetic tool is disposed in the container separately from the polyether-based urethane foam impregnated with the emulsified cosmetic composition.

7. The cosmetic product of claim 1, wherein the emulsified cosmetic composition is make-up primer, make-up base, foundation, powder, twin cake, lipstick, lip gloss, eye shadow, eye brow, concealer, or blusher.

8. The cosmetic product of claim 1, wherein the polyether-based urethane foam is not broken when the polyether-based urethane foam impregnated with a W/O type emulsified cosmetic composition is stored at 55° C. for 7 days.

9. The cosmetic product according to claim 1, wherein the density of the polyether-based urethane foam is 2-3 pcf as determined by ASTM D3547 before the cosmetic composition is impregnated.

10. The cosmetic product according to claim 1, wherein the density of the polyether-based urethane foam is 1-2 pcf as determined by ASTM D3547 before the cosmetic composition is impregnated.

11. A cosmetic product comprising:
an emulsified cosmetic composition;
a polyether-based urethane foam impregnated with the emulsified cosmetic composition; and
a container in which the polyether-based urethane foam impregnated with the emulsified cosmetic composition is stored,
wherein the emulsified cosmetic composition is released from the polyether-based urethane foam impregnated with the emulsified cosmetic composition to a cosmetic tool that is separate from the polyether-based urethane foam and that tool is for applying the released emulsified cosmetic composition to skin, and
wherein the polyether-based urethane foam has a reticulated structure and a pore number of 70-120 pores per inch (ppi) before the emulsified cosmetic composition is impregnated, and wherein the polyether-based urethane foam has a density of 1-3 pounds per cubic foot (pcf) as determined by ASTM D3547 before the emulsified cosmetic composition is impregnated.

12. The cosmetic product of claim 11, wherein the polyether-based urethane foam has a pore number of 75 to 95 pores per inch.

13. The cosmetic product of claim 11, wherein the polyether-based urethane foam has a hardness of 10-70 as determined by a durometer before the cosmetic composition is impregnated.

14. The cosmetic product of claim 11, wherein the emulsified cosmetic composition is a water in oil (W/O) composition or an oil in water (O/W) composition.

15. The cosmetic product of claim 11, wherein the emulsified cosmetic composition has a viscosity of 5,000-15,000 cps.

16. The cosmetic product of claim 11, wherein the emulsified cosmetic composition is a UV-protecting cosmetic composition.

17. The cosmetic product of claim 11, wherein the cosmetic tool is disposed in the container separately from the polyether-based urethane foam impregnated with the emulsified cosmetic composition.

18. The cosmetic product of claim 11, wherein the emulsified cosmetic composition is make-up primer, make-up base, foundation, powder, twin cake, lipstick, lip gloss, eye shadow, eye brow, concealer, or blusher.

19. The cosmetic product of claim 11, wherein the polyether-based urethane foam is not broken when the polyether-based urethane foam impregnated with a W/O type emulsified cosmetic composition is stored at 55° C. for 7 days.

20. The cosmetic product according to claim 11, wherein the density of the polyether-based urethane foam is 2-3 pcf as determined by ASTM D3547 before the cosmetic composition is impregnated.

21. The cosmetic product according to claim 11, wherein the density of the polyether-based urethane foam is 1-2 pcf as determined by ASTM D3547 before the cosmetic composition is impregnated.

22. A method of making the cosmetic product of claim 1 comprising:
impregnating a polyether-based urethane foam with an emulsified cosmetic composition to form an impregnated polyether-based urethane foam; and
storing the impregnated polyether-based urethane foam in a container separately from a cosmetic tool that is for applying the emulsified cosmetic composition released from the impregnated polyether-based urethane foam to skin,
wherein the polyether-based urethane foam has a reticulated structure and a pore number of 70-120 pores per inch (ppi) before the emulsified cosmetic composition is impregnated.

23. A method of making the cosmetic product of claim 11 comprising:
impregnating a polyether-based urethane foam with an emulsified cosmetic composition to form an impregnated polyether-based urethane foam; and
storing the impregnated polyether-based urethane foam in a container separately from a cosmetic tool that is for applying the emulsified cosmetic composition released from the impregnated polyether-based urethane foam to skin,
wherein the polyether-based urethane foam has a reticulated structure.

24. A method of applying an emulsified cosmetic composition to skin comprising:
releasing an emulsified cosmetic composition that is impregnated in a polyether-based urethane foam onto a cosmetic tool that is for applying the emulsified cosmetic composition released from the impregnated polyether-based urethane foam to skin; and
applying the released emulsified cosmetic composition to skin using the cosmetic tool; wherein the polyether-based urethane foam has a reticulated structure and a pore number of 70-120 pores per inch (ppi) before the emulsified cosmetic composition is impregnated, and wherein the polyether-based urethane foam has a density of 1-3 pounds per cubic foot (pcf) as determined by ASTM D3547 before the emulsified cosmetic composition is impregnated.

25. The method of claim 24, wherein the polyether-based urethane foam has a pore number of 75 to 95 pores per inch.

26. The method of claim 24, wherein the polyether-based urethane foam has a hardness of 10-70 as determined by a durometer before the cosmetic composition is impregnated.

27. The method of claim 24, wherein the emulsified cosmetic composition is a water in oil (W/O) composition or an oil in water (O/W) composition.

28. The method of claim 24, wherein the emulsified cosmetic composition has a viscosity of 5,000-15,000 cps.

29. The method of claim 24, wherein the emulsified cosmetic composition is a UV-protecting cosmetic composition.

30. The method of claim 24, wherein the cosmetic tool is disposed in the container separately from the polyether-based urethane foam impregnated with the emulsified cosmetic composition.

31. The method of claim 24, wherein the emulsified cosmetic composition is make-up primer, make-up base, foundation, powder, twin cake, lipstick, lip gloss, eye shadow, eye brow, concealer, or blusher.

32. The method of claim 24, wherein the polyether-based urethane foam is not broken when the polyether-based urethane foam impregnated with a W/O type emulsified cosmetic composition is stored at 55° C. for 7 days.

33. The method of claim 24, wherein the density of the polyether-based urethane foam is 2-3 pcf as determined by ASTM D3547 before the cosmetic composition is impregnated.

34. The method of claim 24, wherein the density of the polyether-based urethane foam is 1-2 pcf as determined by ASTM D3547 before the cosmetic composition is impregnated.

* * * * *